United States Patent [19]

Nakabayashi et al.

[11] Patent Number: 5,264,215
[45] Date of Patent: Nov. 23, 1993

[54] BONE CEMENT COMPOSITION, CURED PRODUCT THEREOF, IMPLANT MATERIAL AND PROCESS FOR THE PREPARATION OF THE SAME

[75] Inventors: Nobuo Nakabayashi, 6-20 Koganehara 5-chome, Matsudo-shi, Chiba 270; Kazuhiko Ishihara, Kodaira; Takashi Yamamoto, Kuga, all of Japan

[73] Assignees: Nobuo Nakabayashi, Chiba; Mitsui Petrochemical Industries, Ltd.; Asahi Kogaku Kogyo Kabushiki Kaisha, both of Tokyo, all of Japan

[21] Appl. No.: 599,827

[22] Filed: Oct. 19, 1990

[30] Foreign Application Priority Data

Oct. 19, 1989 [JP] Japan .................................. 1-272644
Oct. 19, 1989 [JP] Japan .................................. 1-272645

[51] Int. Cl.⁵ .......................... A61F 2/02; A61F 2/28; A61C 13/10; C08L 33/12
[52] U.S. Cl. .................... 424/423; 433/201.1; 433/212.1; 523/115; 623/16
[58] Field of Search .......... 523/115; 424/423; 623/16, 16 A-16 G; 433/201.1, 212.1

[56] References Cited

U.S. PATENT DOCUMENTS

| | | | |
|---|---|---|---|
| 4,373,217 | 2/1983 | Draenert | 433/20 |
| 4,514,527 | 4/1985 | Bowen | 523/115 |
| 4,610,692 | 9/1986 | Eitenmuller et al. | 623/16 |
| 4,636,526 | 1/1987 | Dorman et al. | 523/115 |
| 4,782,826 | 11/1988 | Fogarty | 128/79 |
| 4,985,198 | 1/1991 | Hirasawa et al. | 560/130 |

FOREIGN PATENT DOCUMENTS 0016906  1/1980  European Pat. Off.
0058867  2/1982  European Pat. Off.
3736554 10/1987  Fed. Rep. of Germany.

OTHER PUBLICATIONS

Chemical Abstracts, 96:223195a, Jun. 28, 1982, p. 370, N. Nakabayashi et al.: "Studies on dental self-curing resins. 22. Adhesion of 4-Meta/MMa-TBB Resin to Enamel".

Primary Examiner—Thurman K. Page
Assistant Examiner—Carlos Azpuru
Attorney, Agent, or Firm—Sherman and Shalloway

[57] ABSTRACT

Disclosed is a bone cement composition comprising polyalkyl methacrylate derived from methacrylate having an alkyl group of 1-4 carbon atoms, hydroxyapatite, alkyl methacrylate having an alkyl group of 1-4 carbon atoms, 4-(2-methacryloyloxyethyl)trimellitic acid or anhydride thereof, and a polymerization initiator. Also disclosed are a cured product of the composition, an implant material using the composition and a process for the preparation of the implant material.

12 Claims, 2 Drawing Sheets

FIG 3-a
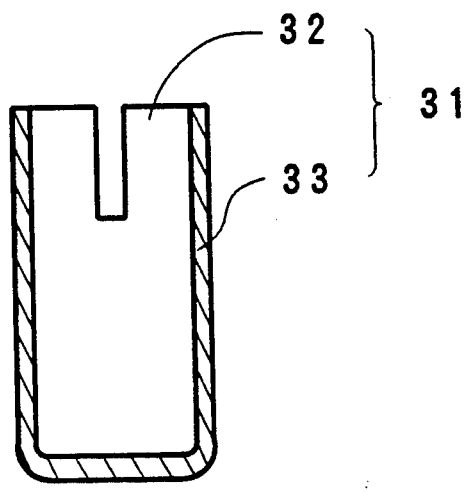
FIG 3-b
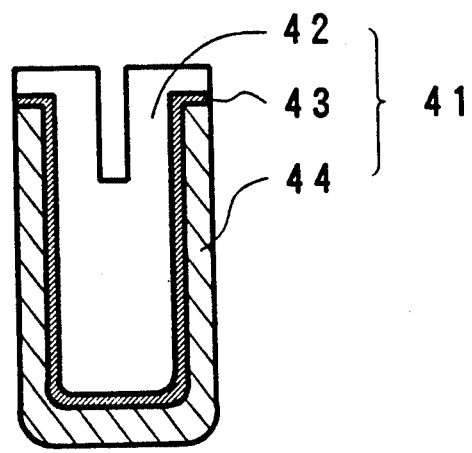

BONE CEMENT COMPOSITION, CURED PRODUCT THEREOF, IMPLANT MATERIAL AND PROCESS FOR THE PREPARATION OF THE SAME

FIELD OF THE INVENTION

The present invention relates to a bone cement composition particularly suitable for adhesion to a natural bone and an artificial bone, and a reaction cured product of the composition.

The invention also relates to an implant material such as an artificial bone, an artificial tooth root (fung) and a process for the preparation of the implant material.

BACKGROUND OF THE INVENTION

After a part of a bone is surgically removed because of disease such as malign tumor or osteomyelitis, a method of transplanting (grafting) an artificial bone formed from a metal instead of the removed bone has been generally adopted. The transplantation (graft) of the artificial bone is made, for example, by providing a cavity in a natural bone for receiving the artificial bone after removing a part of the natural bone, then filling the cavity with a bonding agent, putting the artificial bone into the bonding agent and curing the bonding agent to close the gaps between the natural bone and the artificial bone and adhere them to each other. As the bonding agent, there has been conventionally employed a mixture of methyl methacrylate (referred to hereinafter as "MMA") and a polymerization initiator such as benzoyl peroxide (referred to hereinafter as "BPO") or a mixture of peroxide and a tertiary amine. For curing the bonding agent, the bonding agent is subjected to polymerization reaction at normal temperatures.

However, the cured product shows poor adhesivity to a natural bone, and moreover the curing reaction of MMA is an exothermic reaction, so that the organization of the bone may be denatured owing to the generated heat during the curing reaction of MMA in the case that the reaction is performed at a high speed.

In more detail, when the polymerization reaction of MMA is performed using such a conventional polymerization initiator as a mixture of BPO and amine, the reaction proceeds rapidly to release a reaction heat in a short period of time, so as to temporarily make the temperature of MMA (or cured product of MMA) relatively high. Hence, the organization of the natural bone in contact with the cured product of MMA might be easily denatured.

Further, the cured product of MMA has a low affinity with an organism (i.e., living body), and any substantial adhesive force is not produced between not only the cured product and the artificial bone but also the cured product and the natural bone, so that looseness is brought about with time on each interface therebetween.

For coping with the above-described drawbacks, there has been proposed a method of making the artificial bone itself have a affinity with a natural bone and bonding the surface of the artificial bone to the natural bone grown with time to unite them with each other. That is, the surface of the artificial bone is covered with calcium phosphate such as hydroxyapatite (referred to hereinafter as "HAP") having high affinity with a natural bone to unite the artificial bone to a newborn bone grown with time through calcium phosphate, so as to firmly fix the artificial bone on the natural bone.

However, the method for fixing the artificial bone on the natural bone depending upon a natural healing power of a living body requires a long period of time for growth of a newborn bone, and therefore the affected part must be fixed for that long period of time. The fixing of the affected part for a long time brings about adverse side effect such as reduction of muscular strength or kinetic functions of joints, and in order to recover the reduced functions, rehabilitation of a long period of time is necessary. Such rehabilitation makes the burden too heavy for the patient. Especially for aged persons, such burden is a severe problem because the growth of a newborn bone is slow and a very long time is required for curing the affected part.

Furthermore, since calcium phosphate itself does not have any adhesive force to the artificial bone, it is very important to allow to firmly adhere calcium phosphate to the artificial bone and to cover the artificial bone with calcium phosphate. In the prior arts, the adhesion between the artificial bone and calcium phosphate is insufficient, and various problems still remain accompanied by the insufficient adhesion.

In more detail, for making the artificial bone or artificial tooth root covered with calcium phosphate exhibit the desired functions, it is required that calcium phosphate is firmly adhered to a metal that is a main structural body of the artificial bone or the artificial tooth root. However, most of the artificial bones or artificial tooth roots covered with calcium phosphate are insufficient in this viewpoint. Further, in order to give calcium phosphate a sufficient affinity with organism, it is also required that calcium phosphate has its crystalline structure almost the same as that of the rigid organization of a living body (i.e., natural bone), and that the metal is covered with calcium phosphate of high purity.

For satisfying those requirements, a complex process for preparing the artificial bone or the artificial tooth root is needed, and besides, calcium phosphate is necessarily treated at a high temperature in the process for the preparation. However, even in the case of producing an artificial bone or an artificial tooth root in consideration of the above-mentioned viewpoints, there can be hardly obtained those having satisfactory affinity with organism.

As described above, various problems still reside in both the conventional artificial bone and the conventional artificial tooth root (dental root).

In dentistry for treating teeth having relatively similar organization to that of bones, an adhesive comprising 4-(2-methacryloyloxyethyl)trimellitic anhydride (referred to hereinafter as "4-META") or hydrolyzate thereof (i.e., 4-(2-methacryloyloxyethyl)trimellitic acid, referred to hereinafter as "4-MET"), MMA and tri-n-butylborane (referred to hereinafter as "TBB") has been employed for adhering a metal crown to dentin.

The components of dentin are almost the same as those of a natural bone, so that the present inventors have tried to utilize the adhesion techniques of the dental art in the art of artificial bones. However, even if such techniques are utilized, an adhesive force of the adhesive tends to lower when the adhesive is immersed in water for a long period of time because the affinity of the adhesive with a natural bone is insufficient. For these reasons, it is difficult to firmly adhere an artificial bone to a natural bone without denaturing organization of the natural bone even by the use of the adhesion techniques of dentistry for burying the artificial bone.

OBJECT OF THE INVENTION

The present invention is to solve the above-mentioned problems existing in the prior arts, and it is an object of the invention to provide a bone cement composition capable of favorably bonding an artificial bone formed from for example a metal to a natural bone, and a reaction cured product of the composition.

It is another object of the invention to provide an implant material such as an artificial bone and an artificial tooth root having a high adhesivity to natural bones.

It is a further object of the invention to provide a process for the preparation of the above-mentioned implant material.

SUMMARY OF THE INVENTION

There is provided by the present invention a bone cement composition comprising polyalkyl methacrylate derived from methacrylate having an alkyl group of 1-4 carbon atoms, calcium phosphate such as HAP, alkyl methacrylate having an alkyl group of 1-4 carbon atoms, 4-META or 4-MET, and a polymerization initiator.

There is also provided by the invention a reaction cured product of a bone cement composition comprising polyalkyl methacrylate derived from methacrylate having an alkyl group of 1-4 carbon atoms, calcium phosphate such as HAP, alkyl methacrylate having an alkyl group of 1-4 carbon atoms, 4-META or 4-MET, and a polymerization initiator.

There is further provided by the invention an implant material such as an artificial bone and an artificial tooth root comprising a metal and a cured product of a bone cement composition covering at least a part of a surface of the metal, said composition comprising polyalkyl methacrylate derived from methacrylate having an alkyl group of 1-4 carbon atoms, calcium phosphate such as HAP, alkyl methacrylate having an alkyl group of 1-4 carbon atoms, 4-META or 4-MET, and a polymerization initiator.

There is furthermore provided by the invention a process for the preparation of the above-mentioned implant material comprising the steps of covering at least a part of a surface of a metal with a bone cement composition comprising polyalkyl methacrylate derived from methacrylate having an alkyl group of 1-4 carbon atoms, calcium phosphate such as HAP, alkyl methacrylate having an alkyl group of 1-4 carbon atoms, 4-META or 4-MET, and a polymerization initiator; and curing the covered composition.

BRIEF DESCRIPTION OF THE DRAWINGS

FIG. 1-b is a schematic sectional view illustrating another embodiment of the artificial bones according to the present invention.

FIG. 3-a is a schematic sectional view illustrating one embodiment of the artificial tooth root according to the present invention.

FIG. 3-b is a schematic sectional view illustrating another embodiment of the artificial tooth root according to the present invention.

DETAILED DESCRIPTION OF THE INVENTION

Figure 1A:
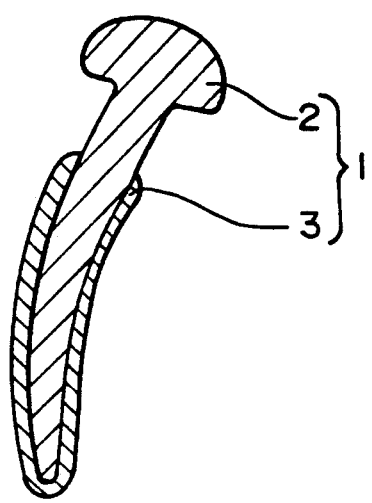
FIG. 1-a is a schematic sectional view illustrating one embodiment of the artificial bones according to the present invention.

A bone cement composition and a reaction cured product of the composition according to the invention are described in detail hereinafter.

A polymer employable as a base for the bone cement composition of the invention (also referred to hereinafter as "base polymer") is polyalkyl methacrylate having an alkyl group of 1-4 carbon atoms.

As the base polymer, there is generally used polyalkyl methacrylate having a molecular weight of $10^3$ to $10^8$, preferably $10^4$ to $10^6$, when measured based on GPC in terms of polystyrene. The polyalkyl methacrylate is preferably employed in the form of a powder.

Examples of the base polymers include poly-MMA, polyethyl methacrylate, polypropyl methacrylate and polybutyl methacrylate. These base polymers can be employed singly or in combination.

Of these base polymers, most preferred is poly-MMA because possibility of harming human bodies is very low.

The bone cement composition of the invention contains calcium phosphate.

The calcium phosphate has a relatively similar component structure to that of a natural bone, so that the calcium phosphate is finally united with a newborn bone in accordance with growth of the bone to produce a high bond strength (high adhesion strength) between the bone cement composition and the bone.

The calcium phosphate used in the present invention include, for example, hydroxyapatite, fluoroapatite, tricalcium phosphate, tetracalcium phospate and a mixture thereof.

The calcium phosphate used in the present invention may be heat treated or not heat treated. Further the calcium phosphate may be porous or not porous.

In the invention, the calcium phosphate of various forms can be employed. Especially when the calcium phosphate having a mean particle diameter of 1 to 20 $\mu$m is used, an adhesion strength between a natural bone and a cured product of the bone cement composition and a compression strength can be prominently enhanced. The calcium phosphate having a mean particle diameter of 2 to 15 $\mu$m is more preferably employed, and thereby a cement composition capable of forming a cured product much more enhanced in the adhesion strength and the compression strength can be obtained.

The calcium phosphate is preferably used in the form of a mixture with a polyalkyl methacrylate powder. In the mixture, the ratio between calcium phosphate and polyalkyl methacrylate is generally within the range of 0.1:99.9 to 90:10, preferably 10:90 to 80:20, (calcium phosphate:polyalkyl methacrylate, by weight).

In the bone cement composition of the invention, alkyl methacrylate having an alkyl group of 1-4 carbon atoms is employed as a polymerizable monomer component. Examples of the alkyl methacrylates include alkyl monomethacrylate such as MMA, ethyl methacrylate, propyl methacrylate and butyl methacrylate; and alkyl dimethacrylate such as ethylene dimethacrylate and propyl dimethacrylate. They can be employed singly or in combination. Of these, preferably employed as the monomer component is MMA because possibility of harming human bodies is very low.

The bone cement composition also contains as a monomer component 4-META or 4-MET having the following formula:

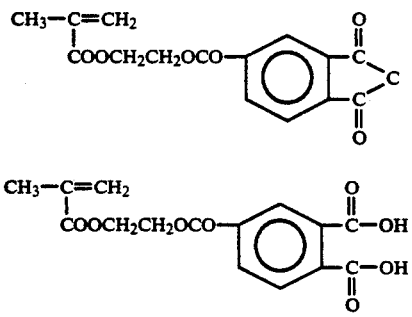

The above-described alkyl methacrylate and 4-META (or 4-MET) are usually used in liquid state, so that it is preferred to beforehand dissolve 4-META (or 4-MET) in the liquid methacrylates separately from the aforementioned polyalkyl methacrylate and calcium phosphate to prepare a mixture liquid (i.e., liquid component (L)). In this case, the liquid component (L) is prepared by mixing alkyl methacrylate and 4-META (or 4-MET) in a ratio of generally 99.9:0.1 to 85:15, preferably 99.5:0.5 to 90:10 (alkyl methacrylate:4-META, by weight). By using those liquid components in the above-mentioned ratio, the adhesion strength of the resulting composition and the strength of a cured product of the composition can be prominently enhanced.

The ratio of the aforementioned solid (powdery) component (P) to the liquid component (L), that is, component (P)/component (L), is generally within the range of 0.01 to 10, preferably 0.1 to 5.

Examples of the polymerization initiators employable in the invention include a redox type polymerization initiator, which is a combination of benzoyl peroxide (BPO) and amine and conventionally used for preparing acrylic polymers at approx. normal temperatures, and alkyl borone. Particularly preferred are tri-n-butylborane (TBB) and/or partially oxidized TBB. In the case of using TBB and/or partially oxidized TBB, the compound reacts with oxygen and water existing in air to generate a radical, and owing to the radical, the polymerization reaction of alkyl methacrylate and 4-META (or 4-MET) in the composition is performed to cure the bone cement composition of the invention.

The polymerization initiator is used in such an amount that the polymerization reaction is brought about. In general, the polymerization initiator is used in an amount of 0.1 to 1 part by weight per 1 part by weight of the total of 4-META (or 4-MET) and alkyl methacrylate. Especially in the case of using TBB as the polymerization initiator, the amount of TBB is preferably in the range of 0.3 to 0.4 part by weight. The amount of TBB in this case is larger than that of a polymerization initiator used for an adhesive composition in dentistry. When TBB is used in the above-mentioned amount and used in combination with 4-META (or 4-MET) and calcium phosphate, the resulting bone cement composition can show curing properties, adhesion strength and compression strength suitable for firmly bonding an artificial bone and a natural bone.

The bone cement composition can be produced by beforehand preparing each components separately and mixing them immediately before the use of the composition, but the composition is advantageously produced by beforehand preparing the solid component, the liquid component and the polymerization initiator as described above and mixing them immediately before the use of the composition. In the latter case, the solid component can be obtained by mixing polyalkyl methacrylate (base polymer) and calcium phosphate. The solid component may contain various additives such as X-ray contrast medium (e.g., barium sulfate), antibiotics and other fillers. Those various additives are preferably sterilized prior to the use thereof. In the case of using a peroxide type polymerization initiator such as benzoyl peroxide as a polymerization initiator, the polymerization initiator can be added to the solid component.

The liquid component can be obtained by mixing alkyl methacrylate and 4-META (or 4-MET) with each other. The liquid component may contain a polymerization inhibitor such as hydroquinone to inhibit the polymerization reaction of the above-described monomer component during the storage. Further, the liquid component may also contain other additives such as antibiotics and X-ray contrast medium. Moreover, the liquid component can contain N,N-dimethyl-p-toluidine for the acceleration of curing the resulting bone cement composition within a living body.

The polymerization initiator is stored and transferred separately from the above-mentioned liquid component. Otherwise, the polymerization initiator is added to the solid component as described above. Especially in the case of using a polymerization initiator which forms a radical upon reaction with oxygen or water in air, such as TBB, the polymerization initiator is generally enclosed with an appropriate sealed container such as an ampule in the storage or transferrence thereof. For example, the solid component, the liquid component and the polymerization initiator which are separately prepared (or separately packaged) from each other are mixed with each other immediately before the use thereof to prepare a bone cement composition of the invention, whereby a curing reaction is initiated. That is, those components are mixed with each other immediately before the used thereof to prepare an employable bone cement composition.

The artificial bone and the artificial tooth root according to the invention are described in detail below.

Figure 1B:
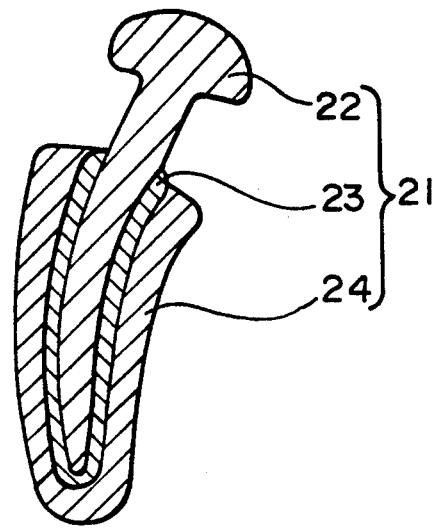

FIG. 1-a is a schematic sectional view showing an embodiment of the artificial bone of the invention.

The artificial bone 1 of the invention comprises a metal 2 and a layer 3 of a cured product (i.e., cured product layer) of a polyalkyl methacrylate composition which covers at least a part of a surface of the metal 2. The polyalkyl methacrylate composition used herein comprises polyalkyl methacrylate derived from methacrylate having an alkyl group of 1–4 carbon atoms, calcium phosphate, alkyl methacrylate having an alkyl group of 1–4 carbon atoms, 4-META or 4-MET, and a polymerization initiator.

As the metal 2 for the artificial bone of the invention, there can be employed a metal which hardly gives an adverse effect to organism even when used for a long period of time and is not varied in its nature for a long period of time. An example of such metal is stainless steel.

The artificial bone of the invention can take various forms depending upon the portion of a living body where the artificial bone is applied. FIG. 1-a shows an artificial bone employable for a hip joint, and the artificial bone can be also employed for other artificial joints such as a knee joint and an ankle joint. Otherwise, the artificial bone can be effectively used for portions of a living body which are connected to other bone organization, such as a tooth root.

On a surface of the metal 2 of the artificial bone 1 according to the invention is provided a cured product layer 3 containing calcium phosphate.

The cured product layer 3 is generally provided whole surface of the metal 2 facing a natural bone, but the layer 3 may be provided on a part of the metal surface facing the natural bone.

The layer 3 is formed from a cured product of a methacrylate resin containing calcium phosphate, and the cured product is concretely a cured product of a resin composition containing a base polymer, calcium phosphate, a monomer component and a polymerization initiator as described above.

The artificial bone of the invention can be prepared by coating the composition containing the above-described calcium phosphate and other components on a surface of a metal 2, or molding the composition in a mold made of Teflon and then curing the composition.

The thickness of the coated layer of the composition can be varied depending on the purpose of the resulting artificial bone. In general, the composition is coated (or covered) in such an amount that the thickness of the cured product layer 3 of the composition would be not smaller than 0.1 $\mu$m, preferably in the range of 1 to 500 $\mu$m.

The coated composition can be cured at normal temperatures or cured under heating.

The shape of the coated layer can be easily varied correspondingly to a shape or a size of a cavity provided in a natural bone for receiving the resulting artificial bone.

The artificial bone prepared as above can be bonded (adhered) to a natural bone using an adhesive (bone cement) having an equivalent composition to that of the bone cement composition used for the cured product layer 3. Otherwise, the artificial bone can be transplanted in the same manner as conventionally employed to be united with a natural bone with time.

The calcium phosphate contained in the cured product layer 3 has a very similar component structure to that of a natural bone, so that a newborn bone is finally united with the calcium phosphate so as to give a prominently high adhesion force between the artificial bone and the natural bone, whereby any looseness does not occur on the adhered portion even when the artificial bone is used for a long period of time.

The artificial bone of the invention comprises a metal and a cured product of a specific composition covering a surface of the metal as described above. However, other embodiment shown in FIG. 1-b is also included in the artificial bone of the invention.

As shown in FIG. 1-b, the artificial bone 21 of the invention comprises a metal 22, a cured product layer 23 of a bone cement composition of the invention and a calcium phosphate layer 24 provided thereon which faces a natural bone. As the metal 22, the same metal as described above (i.e., metal employable for the embodiment described above) can be employed.

The calcium phospate layer 24 can be formed by any conventional methods such as a method of compression molding of calcium phosphate. In detail, the calcium phosphate is subjected to compression molding in such a manner that a cavity for receiving the metal 22 is formed. The calcium phosphate is then subjected to sintering.

The metal 22 and the calcium phosphate layer 24 are combined with each other using a polyalkyl methacrylate composition containing calcium phosphate. The polyalkyl methacrylate composition used herein comprises polyalkyl methacrylate derived from methacrylate having an alkyl group of 1–4 carbon atoms, calcium phosphate, alkyl methacrylate having an alkyl group of 1–4 carbon atoms, 4-META or 4-MET, and a polymerization initiator. Through the cured product layer 23 of the composition, the metal 22 and the calcium phosphate layer 24 are adhered to each other.

The thickness of the cured product layer 23 is generally not smaller than 1 $\mu$m, preferably in the range of 1 to 500 $\mu$m. The thickness of the calcium phosphate layer is generally in the range of 0.1 to 10 mm, preferably 0.1 to 5 mm.

An example of the use of the artificial bone according to the invention is described below.

Figure 2:
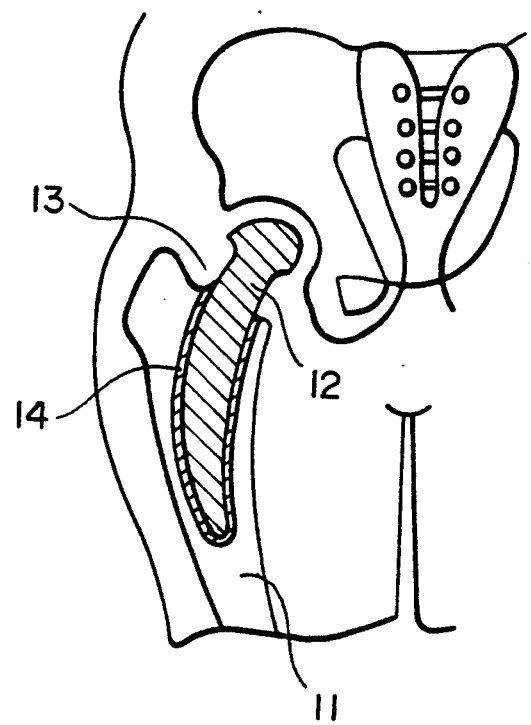
FIG. 2 is a schematic view illustrating a hip joint formed by burying the artificial bone of the present invention into a femur.

FIG. 2 is a schematic view illustrating an example of an artificial hip joint using the artificial bone of the invention.

A femur 11 is provided a cavity 13 for receiving an artificial joint 12, then the cavity 13 is charged with a bone cement composition 14. Subsequently, the artificial joint is inserted into the cavity 13 having been charged with the bone cement composition. In accordance with the curing of the bone cement composition, the artificial joint 12 is adhered to the femur 11 owing to the chemical adhesive force of the bone cement composition. The time required for completion of the adhesion between the artificial joint and the femur is varied depending on the nature of the used bone cement composition. Generally, the time therefor is within the range of approx. 0.5 to 3 hours, and this time is a little longer than the case of using a conventional bone cement composition. Accordingly, a heat-generating temperature of the bone cement composition in the curing stage is low, so that the organization of the femur contacting the bone cement composition is hardly damaged. For this reason, a growth of a newborn bone can be expected. Further, since calcium phosphate contained in the bone cement composition of the invention has a very similar component structure to that of the newborn bone, the calcium phosphate and the natural bone are finally united. In the case of using the bone cement composition of the invention, the femur and the artificial joint can be bonded to each other not only by a chemical adhesive force of the bone cement composition but also by a joining force given by the unification of newborn bone and calcium phosphate, so that looseness between the artificial bone and the femur hardly occurs even in the case of using the artificial bone for a long period of time.

The present invention is described above exemplifying an artificial bone, but the invention is also applicable to an artificial tooth root.

FIG. 3-a is a schematic sectional view showing an embodiment of the artificial tooth root of the invention.

The artificial tooth root 31 of the invention comprises a metal 32 and a cured product layer 33 of a polyalkyl methacrylate composition (i.e., a bone cement composition of the invention) covers at least a part of a surface of the metal 32.

FIG. 3-b is a shematic sectional view showing another embodiment of the artificial tooth root of the invention.

As shown in FIG. 3-b, the artificial tooth root 41 of the invention comprises a metal 42, a cured product layer 43 of a bone cement composition of the invention and a calcium phosphate layer 44 provided thereon which faces a natural bone of jaw. As each of the metals 32, 42, the same metal as described above (i.e., metal employable for the embodiment described above) can be employed. Further, each of the cured product layers 33, 43 and the calcium phosphate layer 44 can also be formed by the same way as described above.

The artificial tooth using the artificial tooth root of the invention can be implanted as follows.

After baring a bone of jaw out of gingiva on which no tooth exists, the bone of jaw is provided a cavity for receiving an artificial tooth root, then the cavity is charged with a bone cement composition. Subsequently, the artificial tooth root is inserted into the cavity having been charged with the bone cement composition to be fixed to the cavity by curing the bone cement composition.

As shown in FIG. 3-a and FIG. 3-b, the metal of the tooth root has a groove opened axially at about the central part on its top.

A protuberance formed at the bottom of an abutment is screwed in the groove, or bonded to the groove with an adhesive. Then the abutment is covered with an crown to form an artificial tooth.

The bone cement composition of the invention can be employed for adhering an artificial joint as described above, and in addition, it can be also employed as a substitution bone by charging it in a broken portion of a natural bone.

EFFECT OF THE INVENTION

The bone cement composition of the invention contains calcium phosphate such as HAP, and the calcium phosphate has a very similar component structure to that of a natural bone, so that the calcium phosphate is united to a newborn bone. Further, the composition contains a specific polyalkyl methacrylate as a host component and thereby shows excellent adhesion properties to a metal, so that any looseness is not brought about between an artificial bone (e.g., artificial joint) and a natural bone even when the artificial bone is used for a long period of time.

By adhering an artificial bone to a natural bone using the bone cement composition of the invention, the growth of a newborn bone is not inhibited, whereby the artificial bone, a natural bone and the cured product of the bone cement composition can be firmly adhered and united to each other for a short period of time. Accordingly, the affected part is not required to be fixed for a long period of time, differently from conventional cases, so that the decline of functions occuring in the vicinity of the affected part is remarkably decreased by using the bone cement composition of the invention.

Moreover, the monomer components such as alkyl methacrylate and 4-META in the bone cement composition of the invention are dissolved out in only a small amount, and hence an adverse effect is hardly given to a human body.

After the bone cement composition of the invention is coated over a surface of a natural bone and then the composition is cured, it has been confirmed by a scanning electron microscope that the bone and the cured product of the bone cement composition are firmly adhered to each other.

The implant material such as the artificial bone or the artificial tooth root according to the invention has on its surface a layer of a cured product of a specific methacrylate resin containing calcium phosphate such as HAP. This calcium phosphate has a very similar component structure to that of a natural bone, so that a newborn bone adsorbs the calcium phosphate to be united in accordance with the growth of the bone. Further, the specific polyalkyl methacrylate shows excellent adhesion properties to metals, and therefore looseness is hardly given between an artificial bone (e.g., artificial joint) and a natural bone even if the artificial bone is used for a long period of time. Furthermore, any complex process is not needed for preparing the implant material of the invention, for example, they can be easily prepared at normal temperatures.

The present invention are further described by the following examples, but those examples are given by no means to restrict the invention.

EXAMPLES 1-4 AND COMPARISON EXAMPLE 1

93 g of polymethylmethacrylate (Acrybase, ME-3F, tradename of Fujikura Kasei Co., Ltd.) and 7 g of barium sulfate were mixed with each other to prepare a powdery polyalkyl methacrylate component.

To 0.8 g of the powdery polyalkyl methacrylate component was added 0.2 g of porous HAP (Ca/P=1.7) having a mean particle diameter of 5 μm (each particle having spherical form), to prepare a solid component (P) containing HAP in an amount of 20% by weight.

Independently, 19.0 g of MMA and 1.0 g of 4-META were mixed with each other to prepare a liquid component (L).

To 0.4 g of the liquid component (L) was added 3 drops (approx. 0.15 to 0.20 g) of TBB, and they were well mixed. To the resulting mixture was further added 1 g of the above-obtained solid component (P), and they were mixed to prepare a bone cement composition of the invention.

Using the bone cement composition prepared as above, two test specimens of cured product of the composition were prepared. One specimen was in the rectangular form having a size of 4.0 mm×4.0 mm×3.0 mm, and the other specimen was in the columnar form having a diameter of 6 mm and a length of 8 mm. Of the two, the former was per se measured on the compression strength, and latter was measured on the compression strength after immersed in water for 2 months, using an autograph (DSS500, produced by Shimazu Seisakusho Co., Ltd.). The value of the compression strength is a value at which each specimen is broken.

The same procedures as described above were repeated except for varying the content of HAP in the solid component (P) to 40% by weight (Example 2), 60% by weight (Example 3) and 80% by weight (Example 4) to prepare various bone cement compositions. Using each of the compositions, test specimens of cured product of the composition were prepared in the same manner as described above. Then, the obtained specimens were measured on the compression strength in the same manner as described above.

Further, the same procedures as described above were repeated except for not using HAP to prepare a composition not containing HAP for comparison. Using the composition, test specimens of cured product of the composition were prepared in the same manner as described above, and the obtained specimens were measured on the compression strength in the same manner as described above.

The results are set forth in Table 1.

EXAMPLES 5-7

The procedures for preparing a bone cement composition in Example 1 were repeated except for using HAP having a mean particle diameter of 15 μm in the amount of 20% by weight (Example 5), 40% by weight (Example 6) and 60% by weight (Example 7) instead of HAP having a mean particle diameter of 5 μm, to prepare various bone cement compositions. Using each of the obtained bone cement compositions, test specimens of cured product of the composition were prepared in the same manner as described in Example 1. Then, the obtained specimens were measured on the compression strength in the same manner as described above.

The results are also set forth in Table 1.

TABLE 1

| | HAP in Solid Component | | Compression Strength (kgf/cm$^2$) | |
|---|---|---|---|---|
| | Particle diameter (μm) | Amount (wt. %) | Dried state | After immersing in water |
| Example 1 | 5 | 20 | 593 | 543 |
| Example 2 | 5 | 40 | 540 | 604 |
| Example 3 | 5 | 60 | 636 | 608 |
| Example 4 | 5 | 80 | 969 | 702 |
| Example 5 | 15 | 20 | 873 | 524 |
| Example 6 | 15 | 40 | 749 | 624 |
| Example 7 | 15 | 60 | — | 646 |
| Com. Ex. 1 | — | 0 | 529 | 513 |

As is evident from the results set forth in Table 1, the compression strength was increased by addition of HAP, and the strength of the cured product had a tendency of being enhanced in accordance with the increase of the amount of HAP. This fact indicates that HAP serves to enhance the compression strength of the cured product. Further, when the amount of HAP is increased, the affinity between a cured product of the bone cement composition and a bone, and therefore in the case of adding HAP in an amount within the range of the present invention, the adhesive strength between the bone cement composition and the bone can be kept for a long period of time.

EXAMPLES 8-10

On a section of a human femur was attached a masking tape to expose 0.22 cm$^2$ of the femur outside.

Then, on an acrylic rod was placed the bone cement composition prepared each of Examples 1 to 3. The acrylic rod was fixed perpendicularly to the exposed portion of the femur through the composition under pressure, and they were allowed to stand for 30 minutes.

Subsequently, the femur bonded to the acrylic rod was immersed in water for 1 day, and thereafter the adhesion strength between the femur and the acrylic rod was measured using an autograph at a crosshead speed of 2 mm/minute.

Further, the adhesion strength between the acrylic rod and a stainless steel (SUS-304) which was one material of artificial bones was measured in the same manner as described above.

The results are set forth in Table 2.

EXAMPLES 11-13 AND COMPARISON EXAMPLE 2

On a section of a human femur was attached a masking tape to expose 0.22 cm$^2$ of the femur outside.

Then, on an acrylic rod was placed the bone cement composition prepared in each of Examples 5 to 7, and the acrylic rod with the composition was bonded to the exposed portion of the femur through the composition by means of pressure welding, and they were allowed to stand for 30 minutes.

Subsequently, the femur bonded to the acrylic rod was immersed in water for 1 day, and thereafter the adhesion strength between the femur and the acrylic rod was measured using an autograph.

Further, the adhesion strength between the acrylic rod and a stainless steel (SUS-304) which was one material of artificial bones was measured in the same manner as described above.

Furthermore, the adhesion strength between the femur and the acrylic rod and between the stainless steel and the acrylic rod in the case of using a composition not containing HAP was also measured for comparison in the same manner as described above.

The results are also set forth in Table 2.

TABLE 2

| | HAP in Solid Component | | Adhesion Strength (MPa) | |
|---|---|---|---|---|
| | Particle diameter (μm) | Amount (wt. %) | Human femur | Stainless steel (SUS-304) |
| Example 8 | 5 | 20 | 4.1 | 7.1 |
| Example 9 | 5 | 40 | 11.1 | 12.0 |
| Example 10 | 5 | 60 | 9.6 | 10.3 |
| Example 11 | 15 | 20 | 25.5 | 7.3 |
| Example 12 | 15 | 40 | 10.3 | 12.2 |
| Example 13 | 15 | 60 | 9.9 | 11.6 |
| Com. Ex. 2 | — | 0 | 8.5 | 7.8 |

EXAMPLES 14 AND 15 AND COMPARISON EXAMPLE 3

The procedures of Example 2 were repeated except for varying the 4-META concentration in the liquid component to 3% by weight (Example 14), 10% by weight (Example 15) and 0% by weight (Comparison Example 3) to prepare various compositions. In the case of using each of the obtained compositions, the adhesion strength between the human femur and the stainless steel (SUS-304) was measured in the same manner as described above.

The results are set forth in Table 3.

TABLE 3

| | 4-META Concentration | Adhesion Strength (MPa) | |
|---|---|---|---|
| | Amount (wt.%) | Human femur | Stainless steel (SUS-304) |
| Example 14 | 3 | 10.8 | — |
| Example 9 | 5 | 11.1 | 12.0 |
| Example 15 | 10 | 7.6 | — |
| Com. Ex. 3 | 0 | 5.7 | 0 |

As is evident from the results set forth in Table 3, 4-META was very effective for adhesion to the human femur and the stainless steel, and showed a high effectiveness when the 4-META concentration was within the range of 3 to 5% by weight.

EXAMPLES 16-18 AND COMPARISON EXAMPLE 4

Each of the bone cement compositions prepared in Examples 1 to 3 was cured into a columnar form (diameter: 6 mm, length: 8 mm).

The columnar cured product was immersed in methanol for 1 week, and then the amount of the monomers (MMA and 4-META) dissolved in the methanol was measured by the use of a liquid chromatograph (WATERS Micro Bordapac 18, MeOH:H$_2$O=7:3, 1 ml/minute).

Further, the amount of the monomers dissolved in the methanol in the case of using a composition not containing HAP was also measured for comparison in the same manner as described above.

The results are set forth in Table 4.

EXAMPLES 19-21

Each of the bone cement compositions prepared in Examples 5 to 7 was cured into a columnar form (diameter: 6 mm, length: 8 mm).

The columnar cured product was immersed in methanol for 1 week, and then the amount of the monomers (MMA and 4-META) dissolved in the methanol was measured in the same manner as described in Example 16.

Further, the amount of the monomers in the case of using a composition not containing HAP was also measured for comparison in the same manner as described above.

The results are also set forth in Table 4.

TABLE 4

| | HAP in Solid Component | | Amount of Monomer (wt. %) | |
|---|---|---|---|---|
| | Particle diameter (μm) | Amount (wt. %) | MMA | 4-META |
| Example 16 | 5 | 20 | 0.32 | 1.09 |
| Example 17 | 5 | 40 | 0.21 | 0.70 |
| Example 18 | 5 | 60 | 0.17 | 0.54 |
| Example 19 | 15 | 20 | 0.32 | 0.82 |
| Example 20 | 15 | 40 | 0.32 | 0.69 |
| Example 21 | 15 | 60 | 0.24 | 0.42 |
| Com. Ex. 4 | — | 0 | 0.48 | 0.84 |

EXAMPLES 22~24

The procedures of Example 1 were repeated except that each of the following porous calcium phosphates was used instead of HAP to obtain a bone cement composition of the invention:

a) tricalcium phosphate (Ca/P=1.50) heat-treated at 950° C. for 4 hrs (Example 22);

b) the mixture of HAP and tricalcium phosphate (Ca/P=1.60) heat-treated at 950° C. for 4 hrs (Example 23); and c) the mixture of HAP and calcium oxide (Ca/P=1.67) heat-treated at 950° C. for 4 hrs (Example 24).

All of the obtained compositions show as good effects as the composition of Example 1.

What is claimed is:

1. A bone cement composition comprising:

a component (P) containing polyalkyl methacrylate derived from methacrylate having an alkyl group of 1-4 carbon atoms and calcium phosphate in amount such that the ratio between the calcium phosphate and the polyalkyl methacrylate is within the range of 0.1:99.9 to 90:10, parts by weight;

a component (L) containing alkyl methacrylate having an alkyl group of 1-4 carbon atoms, and 4-(2-methacryloyloxyethyl)trimellitic acid or anhydride thereof;

and a polymerization initiator.

2. The bone cement composition as claimed in claim 1, wherein said component (L) contains the alkyl methacrylate and 4-(2-methacryloyloxyethyl)trimellitic acid or anhydride thereof in such amount that the ratio between the alkyl methacrylate and the 4-(2-methacryloyloxyethyl)trimellitic acid or anhydride thereof is within the range of 99.9:0.1 to 85:15, parts by weight;

the ratio of the component (P) to the component (L) is within the range of 0.01 to 10; and the amount of the polymerization initiator contained in the composition is within the range of 0.1 to 1 part by weight per 1 part by weight of the component (L).

3. The bone cement composition as claimed in claim 1, wherein the polyalkyl methacrylate is a homopolymer or a copolymer of methacrylate selected from the group consisting of methyl methacrylate, ethyl methacrylate, propyl methacrylate and butyl methacrylate, and the alkyl methacrylate is methyl methacrylate.

4. The bone cement composition as claimed in claim 1 or 2 wherein the calcium phosphate is hydroxyapatite.

5. The bone cement composition as claimed in claim 1, wherein the calcium phosphate is in the form of particles having a mean particle diameter within the range of 1 to 20 μm.

6. The bone cement composition as claimed in claim 1, wherein the polymerization initiator is tri-n-butylborane and/or a partially oxidized product thereof.

7. A reaction cured product of a composition comprising:

a component (P) containing polyalkyl methacrylate derived from methacrylate having an alkyl group of 1-4 carbon atoms and calcium phosphate in an amount such that the ratio between the calcium phosphate and the polyalkyl methacrylate is within the range of 0.1:99.9 to 90:10, parts by weight;

a component (L) containing alkyl methacrylate having an alkyl group of 1-4 carbon atoms and 4-(2-methacryloyloxyethyl)trimellitic acid or anhydride thereof; and a polymerization initiator.

8. The reaction cured product as claimed in claim 7, wherein said component (L) contains the alkyl methacrylate and 4-(2-methacryloyloxyethyl)trimellitic acid or anhydride thereof in such amount that the ratio between the alkyl methacrylate and the 4-(2-methacryloyloxyethyl)trimellitic acid or anhydride thereof is within the range of 99.9:0.1 to 85:15, parts by weight;

the ratio of the component (P) to the component (L) is within the range of 0.01 to 10; and the amount of the polymerization initiator contained in the composition is within the range of 0.1 to 1 part by weight per 1 part by weight of the component (L).

9. The reaction cured product as claimed in claim 7 or 8, wherein the polyalkyl methacrylate is a homopolymer of methyl methacrylate or ethyl methacrylate or a copolymer of methyl methacrylate and ethyl methacrylate and the alkyl methacrylate is methyl methacrylate.

10. The reaction cured product as claimed in claim 7 or 8 wherein the calcium phosphate is hydroxyapatite.

11. The reaction cured product as claimed in claim 7 or 8, wherein the calcium phosphate has a mean particle diameter within the range of 1 to 20 μm.

12. The reaction cured product as claimed in claim 7 or 8, wherein the polymerization initiator is tri-n-butylborane and/or a partially oxidized product thereof.

* * * * *